United States Patent [19]

Tachikawa

[11] Patent Number: 5,281,737
[45] Date of Patent: Jan. 25, 1994

[54] 1-AZA-2-SILACYCLOBUTANE COMPOUNDS AND METHOD FOR THEIR PREPARATION

[75] Inventor: Mamoru Tachikawa, Kanagawa, Japan

[73] Assignee: Dow Corning Japan, Ltd., Tokyo, Japan

[21] Appl. No.: 86,747

[22] Filed: Jul. 1, 1993

[30] Foreign Application Priority Data

Jul. 6, 1992 [JP] Japan .................................. 4-178491

[51] Int. Cl.$^5$ ................................................ C07F 7/10
[52] U.S. Cl. ...................................................... 556/407
[58] Field of Search ............................................ 556/407

[56] References Cited

U.S. PATENT DOCUMENTS 3,170,941  2/1965  Speier ................................. 556/407
3,532,728 10/1970  Fink ................................... 556/407

FOREIGN PATENT DOCUMENTS 235891  9/1990  Japan .

Primary Examiner—Paul F. Shaver
Attorney, Agent, or Firm—William F. Boley

[57] ABSTRACT

The present invention introduces novel 1-aza-2-silacyclobutane compounds whose nitrogen is substituted by a hydrocarbon group or heteroatom-containing hydrocarbon group, whose N—Si bond remains highly reactive, and which are very effective as silanol endblocking agents and silane coupling agents. The present invention also introduces a method for the preparation of these novel 1-aza-2-silacyclobutanes by the intramolecular hydrosilylation reaction of N,N-disubstituted aminosilane.

9 Claims, No Drawings

1-AZA-2-SILACYCLOBUTANE COMPOUNDS AND METHOD FOR THEIR PREPARATION

BACKGROUND OF INVENTION

The present invention relates to 1-aza-2-silacyclobutane compounds whose nitrogen is substituted by a hydrocarbon group or a hydrocarbon group that contains a heteroatom-containing functional group. The present invention also relates to a method for the preparation of these compounds.

The 1-aza-2-silacyclobutane compounds known to date include 1-aza-2-silacyclobutane compounds in which carbon is bonded to the nitrogen in the 4-membered ring and 1-aza-2-silacyclobutane compounds in which silicon is bonded to this ring nitrogen. N-(1,1-dimethylethyl)-2,2,6-trimethyl-8-phenyl-1-aza-8-silabicyclo[4.2.0]octane-8-amine is an example of the former type of compound. This compound contains some very sterically bulky substituents in order to improve the stability of intermediates generated during its synthesis, but this tactic also reduces the reactivity of this azasilacyclobutane. Furthermore, the synthesis of this compound involves the combination of a number of equivalent reactions, and this compound is problematic from an industrial perspective because of the problem of dealing with by-products as well as the number of steps in its production process. Finally, this azasilacyclobutane is very expensive because the starting reagents used in its synthesis cannot be acquired on an industrial basis.

1-Benzyl-2,2,4-triphenyl-3-isopropyl-1-aza-2-silacyclobutane is another 1-aza-2-silacyclobutane in which carbon is bonded at the 1 position. Due to the extensive introduction of bulky substituents for the purpose of precursor stabilization, this 1-aza-2-silacyclobutane has bulky substituents bonded on all the atoms in the 4-membered ring, and this again results in a loss of reactivity. This azasilacyclobutane is also very expensive because the starting compounds for the precursors cannot be acquired on an industrial basis.

With regard to 1-aza-2-silacyclobutanes in which Si is bonded to the nitrogen in the four-membered ring, Japanese Patent Application Laid Open {Kokai or Unexamined} Number Hei 2-235891 [235,891/1990] discloses the following compound

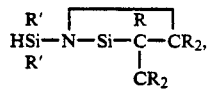

where R is a hydrocarbon group or hydrogen atom and R' is a hydrocarbon group, as a point of departure for the facile stereospecific preparation of 2-amino alcohols by desilylation. According to this invention, 2-amino alcohols are synthesized utilizing the facile hydrolyzability of the two Si—N bonds in the above compound and conversion of the Si—C bond into the Si—O bond by oxidation. Because this compound contains two readily hydrolyzable Si—N bonds, it is difficult to orient cleavage to a particular Si—N bond. When this compound is used, for example, as an endblocker for silanol-terminated siloxane, the following two species are produced, thus creating the problem of by-products:

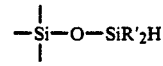

and

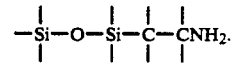

Moreover, because the substituent group on the nitrogen has the —SiR'$_2$H structure, any functional group introduced in R' is subject to limitations imposed by the behavior of the Si—N bond. For example, even when a group such as the allyl group is introduced as R', this R' substituent will not be retained in the azasilacyclobutane skeleton and thus cannot be effectively utilized as a functional group in practical applications due to the facile cleavability of the Si—N bond by such reactions as hydrolysis.

The present invention introduces novel 1-aza-2-silacyclobutane compounds whose nitrogen is substituted by a hydrocarbon group or heteroatom-containing hydrocarbon group, whose N—Si bond is highly reactive, and which are very effective as silanol endblocking agents and silane coupling agents. The present invention also introduces a method for the preparation of these novel 1-aza-2-silacyclobutanes.

Furthermore, because a wide selection of N-bonded functional groups is possible for the 1-aza-2-silacyclobutane compounds of the present invention, these compounds are very useful as the corresponding silane coupling agents and endblockers for polysiloxanes, for example, as in the case of allyl, phenyl, substituted phenyl, benzyl, substituted benzyl, and so forth.

Finally, the preparative method of the present invention makes possible the direct, high yield, and highly selective production, from the dihydrocarbylsilyl derivatives of secondary allylamines, of 1-aza-2-silacyclobutane compounds having a functional group bonded to the nitrogen through carbon.

SUMMARY OF INVENTION

The present invention introduces novel 1-aza-2-silacyclobutane compounds whose nitrogen is substituted by a hydrocarbon group or heteroatom-containing hydrocarbon group, whose N—Si bond remains highly reactive, and which are very effective as silanol endblocking agents and silane coupling agents. The present invention also introduces a method for the preparation of these novel 1-aza-2-silacyclobutanes by the intramolecular hydrosilylation reaction of N,N-disubstituted aminosilane.

DESCRIPTION OF INVENTION

The present invention introduces novel 1-aza-2-silacyclobutane compounds whose nitrogen is substituted by a hydrocarbon group or heteroatom-containing hydrocarbon group, whose N—Si bond remains highly reactive, and which are very effective as silanol endblocking agents and silane coupling agents. The present invention also introduces a method for the preparation of these novel 1-aza-2-silacyclobutanes.

The first embodiment of the present invention comprises 1-aza-2-silacyclobutane compounds described by formula (I)

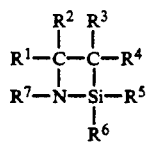
(I)

where $R^1$, $R^2$, and $R^3$ are independently selected from a group consisting of hydrogen and alkyls comprising one to three carbon atoms; $R^4$, $R^5$, and $R^6$ are independently selected from a group consisting of alkyls comprising one to three carbon atoms; and $R^7$ is an organic group selected from a group consisting of (i) saturated or unsaturated monovalent hydrocarbon groups comprising one to 14 carbon atoms and (ii) groups described by formula —$R^{10}$— A in which $R^{10}$ is a saturated or unsaturated divalent hydrocarbon group comprising one to 13 carbon atoms, A is a saturated or unsaturated monovalent organic group comprising one to 13 carbon atoms that contains at least one atom selected from a group consisting of nitrogen, oxygen, sulfur, silicon, fluorine, chlorine, bromine, and iodine, and the sum of the number of carbon atoms in $R^{10}$ and the number of carbon atoms in A is one to 14.

The second embodiment of the present invention comprises a method for the preparation of compounds in accordance with the first embodiment that consists of the execution of an intramolecular hydrosilylation reaction on N,N-disubstituted aminosilane described by formula (II)

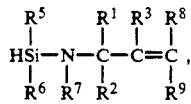
(II)

where $R^1$, $R^2$, $R^3$, $R^5$, $R^6$, and $R^7$ are defined as in the first embodiment, and $R^8$ and $R^9$ are independently selected from a group consisting of hydrogen, methyl, and ethyl with the proviso that when either $R^8$ or $R^9$ is ethyl the other is hydrogen.

The third embodiment of the present invention comprises a method for the preparation of compounds in accordance with the first embodiment that consists of the preparation of N,N-disubstituted aminosilane described by formula (II) in the second embodiment by silylation of secondary amine compounds described by formula (III)

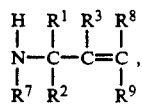
(III)

where $R^1$, $R^2$, $R^3$, and $R^7$ are as defined in the first embodiment and $R^8$ and $R^9$ are as defined in the second embodiment, with silane described by formula (IV)

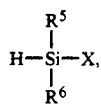
(IV)

where $R^5$ and $R^6$ are as defined in the first embodiment and X is a halogen atom, followed by execution of the method of the second embodiment.

The present invention was achieved as the result of research by the present inventor into compounds described by preceding formula (II). Methyl, ethyl, propyl, and isopropyl comprise the hydrocarbon groups represented by $R^1$, $R^2$, $R^3$, $R^5$, and $R^6$ in formulas (I) through (IV).

$R^1$, $R^2$, $R^3$, $R^8$, and $R^9$ are preferably hydrogen or methyl based on considerations of ease of acquisition of the starting secondary amine and obtaining a high reactivity in the azasilacyclobutane product.

$R^7$ includes alkyl groups such as methyl, ethyl, propyl, isopropyl, butyl, and hexyl; alkenyl groups such as vinyl, allyl, and propenyl; aralkyl groups such as benzyl and substituted benzyl; aryl groups such as phenyl and tolyl; the 2-aminoethyl group; and substituents that themselves contain the azasilacyclobutane structure, as described by the following formulas (V) and (VI):

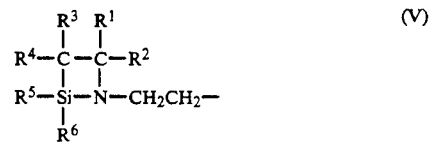
(V)

and

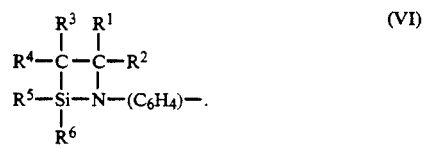
(VI)

Azasilacyclobutanes in accordance with the present invention are exemplified by 1-allyl-2,2,3-trimethyl-1-aza-2-silacyclobutane, 1-(gamma-trimethoxysilylpropyl)-2,2,3-trimethyl-1-aza-2-silacyclobutane, 1-phenyl-2,2,3-trimethyl-1-aza-2-silacyclobutane, 1-benzyl-2,2,3-trimethyl-1-aza-2-silacyclobutane, 1-vinylbenzyl-2,2,3-trimethyl-1-aza-2-silacyclobutane, and the following formulas (VII) and (VIII):

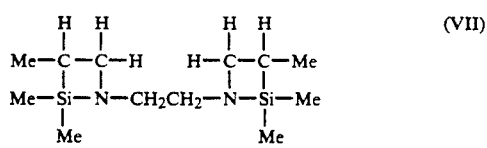
(VII)

and

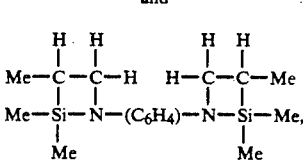

where Me is methyl.

In the 1-aza-2-silacyclobutane compounds according to the present invention, any functional group is bonded to the nitrogen atom through carbon. Moreover, the Si—N bond in the four-membered ring of the 1-aza-2-silacyclobutanes of the present invention undergoes hydrolysis very readily and is easily cleaved. As a consequence, when these compounds are used, for example, as an endblocking agent for silanol-terminated polysiloxanes, endblocking can be realized without the generation of by-products simply by mixing the siloxane with the invention compound.

The present invention will be explained in greater detail in the following examples, but the invention is not limited to these examples. Also, in the following examples, unless expressly indicated otherwise, "part" means "weight part" and "%" means "mol %". For the examples provided, the products were isolated and purified by distillation or preparative gas chromatography, and their structures were confirmed by $^1$H-NMR, $^{13}$C-NMR, $^{29}$Si-NMR, and mass spectrometric analysis, as appropriate.

REFERENCE EXAMPLE 1

Preparation of N-dimethylsilyldiallylamine

Into a nitrogen-flushed vessel were introduced 21 parts diallylamine, 29 parts triethylamine, and 200 parts heptane, and, while agitating, a mixture of 50 parts heptane and 22 parts dimethylchlorosilane was slowly dripped in. After 2 days, another 200 parts heptane was added, and the mixture was filtered to remove the precipitate. The filtrate was distilled to obtain N- dimethylsilyldiallylamine in a yield of 84% based on diallylamine.

REFERENCE EXAMPLE 2

Preparation of N-dimethylsilyl-N-allylaniline

Into a nitrogen-flushed container were introduced 25 parts N-allylaniline, 28 parts triethylamine, and 200 parts hexane, and, while agitating, a mixture of 25 parts dimethylchlorosilane was slowly dripped in. The resulting slurry was heated at reflux for 18 hours, cooled to room temperature, and filtered to remove the precipitate. The filtrate was distilled to obtain N-dimethylsilyl-N-allylaniline in a yield of 64% based on N-allylaniline.

REFERENCE EXAMPLE 3

Preparation of N-dimethylsilyl-N-benzylallylamine

Into a nitrogen-flushed container were introduced 18 parts N-benzylaniline and 50 parts ethyl ether, and while cooling in a water bath 74 parts n-butyllithium/hexane (1.6 mol/L) was slowly dripped in. Then, 11.5 parts dimethylchlorosilane was slowly dripped in. The resulting precipitate was filtered, and the filtrate was distilled to give N-dimethylsilyl-N-benzylallylamine in a yield of 85% based on N-benzylaniline.

EXAMPLE 1

Into a nitrogen-flushed container were introduced 1 part N-dimethylsilyldiallylamine, 3 parts benzene, and 0.003 part bis(triphenylphosphine)dichloroplatinum (PtCl$_2$(PPh$_3$)$_2$), and the mixture was heated at reflux in an oil bath for 4 hours. According to gas chromatographic analysis, no N-dimethylsilyldiallylamine was observed; 1-allyl-2,2,3-trimethyl-1-aza-2-silacyclobutane and 1-allyl-2,2-dimethyl-1-aza-2-silacyclopentane were produced in a molar ratio of 83:17 and a combined yield of 77 mol %. A mixture of these two products was obtained at a yield of 70% by reduced pressure distillation.

EXAMPLE 2

Into a glass tube with an outside diameter of 10 mm and a length of 10 cm were introduced 0.002 mL of a 20 weight % isopropanolic chloroplatinic acid solution and 2 mL of a mixture of 1 part N-dimethylsilyldiallylamine and 3 parts benzene, and the tube was sealed. After this was heated for 17 hours at 80° C., the conversion was 100 weight %. 1-Allyl-2,2,3-trimethyl-1-aza-2-silacyclobutane and 1-allyl-2,2-dimethyl-1-aza-2-silacyclopentane were produced in a molar ratio of 66:34 and a combined yield of 55%.

EXAMPLES 3 to 9

Sealed tube reactions were run as in Example 2 using different platinum catalysts from those used in Examples 1 and 2. The reaction conditions and reaction products are reported in Table 1.

TABLE 1

| example number | catalyst* | silylated amine (g) | solvent (g) | temperature (°C.) | time (hr) | conversion (%) | yield of (I) (%) | ASCP yield** (%) |
|---|---|---|---|---|---|---|---|---|
| 3 | platinum complex #1 | 0.5 | 1.0 | 80 | 13 | 97 | 62 | 22 |
| 4 | platinum complex #2 | 0.5 | 1.0 | 80 | 61 | 100 | 71 | 13 |
| 5 | platinum complex #3 | 0.5 | 1.0 | 100 | 61 | 96 | 81 | 7 |
| 6 | platinum complex #4 | 0.5 | 1.0 | 100 | 15 | 100 | 59 | 17 |
| 7 | platinum complex #5 | 0.5 | 1.0 | 81 | 15 | 100 | 35 | 21 |
| 8 | platinum complex #6 | 0.5 | 1.0 | 80 | 2.5 | 81 | 65 | 14 |
| 9 | platinum complex #7 | 0.5 | 1.0 | 60 | 16 | 100 | 52 | 26 |

*platinum complex #1 = 1 mg Karstedt's catalyst (platinum content = 8.6 weight %) + triisopropyl phosphite (Pt:P molar ratio = 1:2)
platinum complex #2 = 1 mg Karstedt's catalyst (platinum content = 8.6 weight %) + tri-n-butylphosphine (Pt:P molar ratio = 1:2)
platinum complex #3 = 1 mg Karstedt's catalyst (platinum content = 8.6 weight %) + trimethyl phosphite (Pt:P molar ratio = 1:2)
platinum complex #4 = 1 mg Karstedt's catalyst (platinum content = 8.6 weight %) + trimethyl phosphite (Pt:P molar ratio = 1:2)
platinum complex #5 = 1 mg Karstedt's catalyst (platinum content = 8.6 weight %) + trimethyl phosphite (Pt:P molar ratio = 1:1)
platinum complex #6 = 1 mg Karstedt's catalyst (platinum content = 8.6 weight %) + triphenylphosphine (Pt:P molar ratio = 1:5)
platinum complex #7 = 1 mg Karstedt's catalyst (platinum content = 8.6%)
**ASCP = 1-allyl-2,2-dimethyl-1-aza-2-silacyclopentane

EXAMPLES 10

A sealed glass tube reaction was carried out as in Example 2, but in the present case using 10 mg platinum on activated carbon (5 weight % Pt/C) and 2 mL of a mixture of N-dimethylsilyl-N-benzylallylamine and benzene (molar ratio 38:62) and reacting the mixture for 15 hours at 60° C. The conversion of the starting material was 100 weight %. The yield of 1-benzyl-2,2,3-trimethyl-1-aza-2-silacyclobutane was 84% and that of 1-benzyl-2,2-dimethyl-1-aza-2-silacyclopentane was 16%.

EXAMPLE 11

A sealed glass tube reaction was carried out as in Example 2, but in this case using 2 mg bis(triphenylphosphine)dichloroplatinum (PtCl$_2$(PPh$_3$)$_2$) and 2 mL of a mixture of N-dimethylsilyl-N-benzylallylamine and benzene (molar ratio 38:62) and reacting for 15 hours at 60° C. The conversion of starting material was 95%. The yield of 1-benzyl-2,2,3-trimethyl-1-aza-2-silacyclobutane was 92% and that of 1-benzyl-2,2-dimethyl-1-aza-2-silacyclopentane was 2%.

EXAMPLE 12

A sealed glass tube reaction was carried out as in Example 2, but in this case using 2 mg bis(triphenylphosphine)dichloroplatinum (PtCl$_2$(PPh$_3$)$_2$) and 2 mL of a mixture of N-dimethylsilyl-N-allylaniline and benzene (molar ratio 40:60) and reacting for 9 hours at 80° C. The conversion of starting material was 100 weight %. The yield of 1-phenyl-2,2,3-trimethyl-1-aza-2-silacyclobutane was 94% and that of 1-phenyl-2,2-dimethyl-1-aza-2-silacyclopentane was 2%.

The results from hydrosilylation reactions using non-platinum catalysts are given below for the purposes of comparison.

COMPARISON EXAMPLE 1

Into a nitrogen-flushed vessel were introduced 1 part N-dimethylsilyldiallylamine, 3 parts benzene, and 0.003 part tris(triphenylphosphine)chlororhodium (RhCl(PPh$_3$)$_3$) The mixture was heated at reflux for 4 hours in an oil bath. According to gas chromatographic analysis, no N-dimethylsilyldiallylamine was observed. 1-Allyl-2,2-dimethyl-1-aza-2-silacyclopentane and 1-propenyl-2,2-dimethyl-1-aza-2-silacyclopentane were produced in a molar ratio of 98:2 and a combined yield of 95%.

COMPARISON EXAMPLE 2

Into a glass tube with an outside diameter of 10 mm and a length of 10 cm were introduced 2 mg RhCl(PPh$_3$)$_3$ and 2 mL of a mixture of 1 part N-dimethylsilyldiallylamine and 3 parts benzene, and the tube was sealed. After heating this for 17 hours at 80° C., The conversion was 100 weight % and 1-propenyl-2,2-dimethyl-1-aza-2-silacyclopentane was obtained in a yield of 98%. No production of 1-allyl-2,2-dimethyl-1-aza-2-silacyclopentane was observed.

COMPARISON EXAMPLE 3

A sealed glass tube reaction was carried out as in Comparison Example 2 using 2 mg tris(triphenylphosphine)chlororhodium (RhCl(PPh$_3$)$_3$) and 2 mL of a mixture of N-dimethylsilyl-N-benzylallylamine and benzene (molar ratio 38:62) and reacting for 9 hours at 80° C. The conversion of starting material was 100 weight %, and the yield of 1-benzyl-2,2-dimethyl-1-aza-2-silacyclopentane was 98%. No isomeric azasilacyclobutane was produced.

COMPARISON EXAMPLE 4

A sealed glass tube reaction was carried out as in Comparison Example 2 using 2 mg tris(triphenylphosphine)chlororhodium (RhCl(PPh$_3$)$_3$) and 2 mL of a mixture of N-dimethylsilyl-N-allylaniline and benzene (molar ratio 40:60) and reacting for 15 hours at 60° C. The conversion of starting material was 100 weight %. The yield of 1-phenyl-2,2,3-trimethyl-1-aza-2-silacyclobutane was 4%, and that of 1-phenyl-2,2-dimethyl-1-aza-2-silacyclopentane was 72%.

I claim:

1. 1-Aza-2-silacyclobutane compounds described by formula

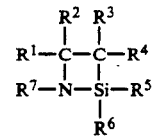

where R$^1$, R$^2$, and R$^3$ are independently selected from a group consisting of hydrogen and alkyls comprising one to three carbon atoms; R$^4$, R$^5$, and R$^6$ are independently selected from a group consisting of alkyls comprising one to three carbon atoms; and R$^7$ is an organic group selected from a group consisting of (i) saturated or unsaturated monovalent hydrocarbon groups comprising one to 14 carbon atoms and (ii) groups described by formula —R$^{10}$— A in which R$^{10}$ is a saturated or unsaturated divalent hydrocarbon group comprising one to 13 carbon atoms, A is a saturated or unsaturated monovalent organic group comprising one to 13 carbon atoms that contains at least one atom selected from a group consisting of nitrogen, oxygen, sulfur, silicon, fluorine, chlorine, bromine, and iodine, and the sum of the number of carbon atoms in R$^{10}$ and the number of carbon atoms in A is one to 14.

2. A method for preparation of 1-aza-2-silacyclobutane described by formula

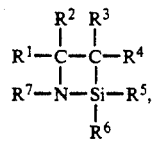

the method comprising: an intramolecular hydrosilylation reaction on N,N-disubstituted aminosilane described by formula

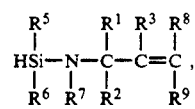

where R$^1$, R$^2$, and R$^3$ are independently selected from a group consisting of hydrogen and alkyls comprising one to three carbon atoms; R$^4$, R$^5$, and R$^6$ are independently selected from a group consisting of alkyls comprising one to three carbon atoms; and R$^7$ is an organic group selected from a group consisting of (i) saturated or unsaturated monovalent hydrocarbon groups comprising one to 14 carbon atoms and (ii) groups described by formula —R$^{10}$— A in which R$^{10}$ is a saturated or unsaturated divalent hydrocarbon group comprising one to 13 carbon atoms, A is a saturated or unsaturated monovalent organic group comprising one to 13 carbon atoms that contains at least one atom selected from a group consisting of nitrogen, oxygen, sulfur, silicon, fluorine, chlorine, bromine, and iodine, and the sum of the number of carbon atoms in R$^{10}$ and the number of carbon atoms in A is one to 14; R$^8$ and R$^9$ are independently selected from a group consisting of hydrogen, methyl, and ethyl, with the proviso that when either $R^8$ or $R^9$ is ethyl the other is hydrogen.

3. A method for preparation of 1-aza-2-silacyclobutane described by formula

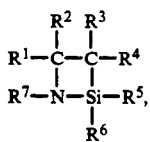

the method comprising: silylating a secondary amine described by formula

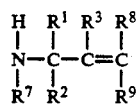

with a silane described by formula

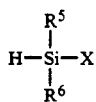

to form a N,N-disubstituted aminosilane described by formula

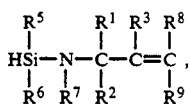

and an intramolecular hydrosilylation reaction of the N,N-disubstituted aminosilane; where $R^1$, $R^2$, and $R^3$ are independently selected from a group consisting of hydrogen and alkyls comprising one to three carbon atoms; $R^4$, $R^5$, and $R^6$ are independently selected from a group consisting of alkyls comprising one to three carbon atoms; $R^7$ is an organic group selected from a group consisting of (i) saturated or unsaturated monovalent hydrocarbon groups comprising one to 14 carbon atoms and (ii) groups described by formula —$R^{10}$— A in which $R^{10}$ is a saturated or unsaturated divalent hydrocarbon group comprising one to 13 carbon atoms, A is a saturated or unsaturated monovalent organic group comprising one to 13 carbon atoms that contains at least one atom selected from a group consisting of nitrogen, oxygen, sulfur, silicon, fluorine, chlorine, bromine, and iodine, and the sum of the number of carbon atoms in $R^{10}$ and the number of carbon atoms in A is one to 14; and $R^8$ and $R^9$ are independently selected from a group consisting of hydrogen, methyl, and ethyl, with the proviso that when either $R^8$ or $R^9$ is ethyl, the other is hydrogen.

4. A method according to claim 2 further comprising the use of a platinum-containing catalyst.

5. A method according to claim 4, where the platinum-containing catalyst is selected from a group consisting of platinum metal, carrier-supported platinum metal, colloidal platinum metal, a zero-valent platinum complex, a divalent platinum complex, and a tetravalent platinum complex.

6. A method according to claim 3 further comprising the use of a platinum-containing catalyst.

7. A method according to claim 6, where the platinum-containing catalyst is selected from a group consisting of platinum metal, carrier-supported platinum metal, colloidal platinum metal, a zero-valent platinum complex, a divalent platinum complex, and a tetravalent platinum complex.

8. A 1-aza-2-silacyclobutane compound according to claim 1 selected from a group consisting of: 1-allyl-2,2,3-trimethyl-1-aza-2-silacyclobutane, 1-(gamma-trimethoxysilylpropyl)-2,2,3-trimethyl-1-aza-2-silacyclobutane, 1-phenyl-2,2,3-trimethyl-1-aza-2-silacyclobutane, 1-benzyl-2,2,3-trimethyl-1-aza-2-silacyclobutane, 1-vinylbenzyl-2,2,3-trimethyl-1-aza-2-silacyclobutane,

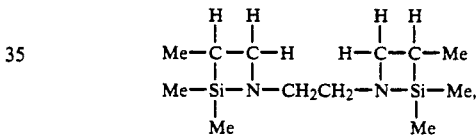

and

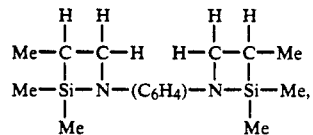

where Me is methyl.

9. A method for preparation of 1-aza-2-silacyclobutane according to claim 3, where the silane is dimethylchlorosilane.

* * * * *